United States Patent [19]

Maijer et al.

[11] 4,424,029
[45] Jan. 3, 1984

[54] LINGUAL PLACEMENT DEVICE

[75] Inventors: Rolf Maijer, Ladysmith; James U. Starck, Victoria, both of Canada

[73] Assignee: Baxter Travenol Laboratories, Inc., Deerfield, Ill.

[21] Appl. No.: 383,712

[22] Filed: Jun. 1, 1982

[51] Int. Cl.³ .............................................. A61C 7/00
[52] U.S. Cl. ........................................................ 433/3
[58] Field of Search ....................................... 433/2, 3

[56] References Cited

U.S. PATENT DOCUMENTS

| | | | |
|---|---|---|---|
| 3,686,762 | 8/1972 | Sutter | 433/3 |
| 3,871,098 | 3/1975 | Dean | 433/3 |
| 4,035,919 | 7/1977 | Cusato | 433/3 |

Primary Examiner—Robert Peshock
Attorney, Agent, or Firm—Paul C. Flattery; Garrettson Ellis

[57] ABSTRACT

A lingual placement device for positioning orthodontic attachments, such as, brackets, on the lingual side of teeth is described. The device includes a handle which is pivoted to a handle extension to permit access to both anterior and posterior teeth in the mouth of a patient. A tooth engagement plate, which engages the front side of a tooth, is pivoted about a horizontal transverse axis. An orthodontic bracket holder is mounted to the handle extension for both horizontal and vertical movement to permit placement of an orthodontic bracket on the lingual side of a tooth. In operation, the tooth engagement plate is positioned in engagement with the front side of the tooth, the bracket is located in its desired position adjacent the lingual side of the tooth by up and down movement of the handle and vertical movement of the bracket holder. The bracket, to which adhesive is applied, is drawn into engagement with the lingual side of the tooth to grip the tooth between the front plate and the bracket until the adhesive has cured sufficiently to adhere the bracket to the tooth. The bracket then is released and the device is removed from the mouth.

11 Claims, 6 Drawing Figures

LINGUAL PLACEMENT DEVICE

FIELD OF INVENTION

The present invention relates to a lingual placement device for positioning orthodontic brackets on the lingual side of teeth.

BACKGROUND TO THE INVENTION

The placement of orthodontic brackets on teeth requires the exercise of considerable skill and accuracy. A variety of positioning instruments are available to place brackets on the outer surface of teeth.

More recently, a new orthodontic technique has been utilized in which orthodontic attachments are made on the tongue or lingual side of the teeth. A transfer tray is currently available to locate one or more brackets on the inside of teeth.

The fabrication of transfer trays for single teeth is both time consuming and expensive but such trays are utilized in the absence of an adequate alternative.

SUMMARY OF INVENTION

In accordance with the present invention, there is provided a lingual placement instrument or device which is able to accurately and positively hold and position orthodontic attachments, including brackets, tubes and auxiliaries, at various vertical heights on both anterior and posterior teeth.

The instrument of the invention includes a tooth engaging plate mounted to a handle of the instrument for engagement with the front side of a tooth and an orthodontic attachment holder independently connected to the handle for bringing an orthodontic attachment into engagement with the lingual side of a tooth and for gripping the attachment to the tooth between the holder and the plate.

The orthodontic attachment holder is independently movable both in a horizontal direction towards and away from the tooth engaging plate so as to bring an orthodontic attachment into engagement with the lingual side of a tooth when the plate is in engagement with the front side of the tooth and in a vertical direction for positioning the orthodontic attachment at a desired vertical location on the lingual side of the tooth.

BRIEF DESCRIPTION OF DRAWINGS

FIG. 3 is a detail perspective view of an alternative attachment holding means for a lingual placement device constructed in accordance with a second embodiment of the invention;

DESCRIPTION OF PREFERRED EMBODIMENTS

Figure 1:
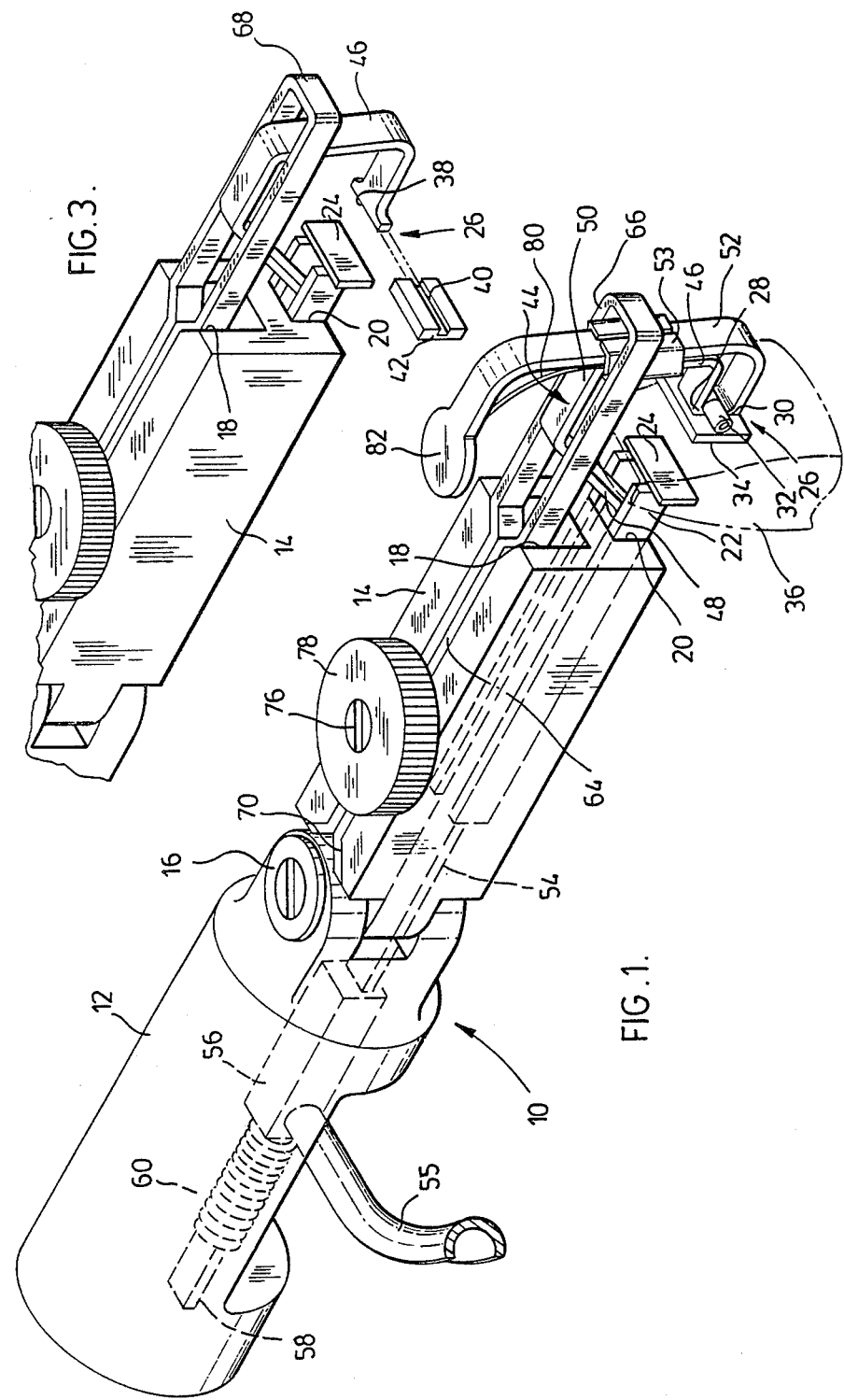
FIG. 1 is a perspective view of a lingual placement device constructed in accordance with one embodiment of the invention.
Figure 2:
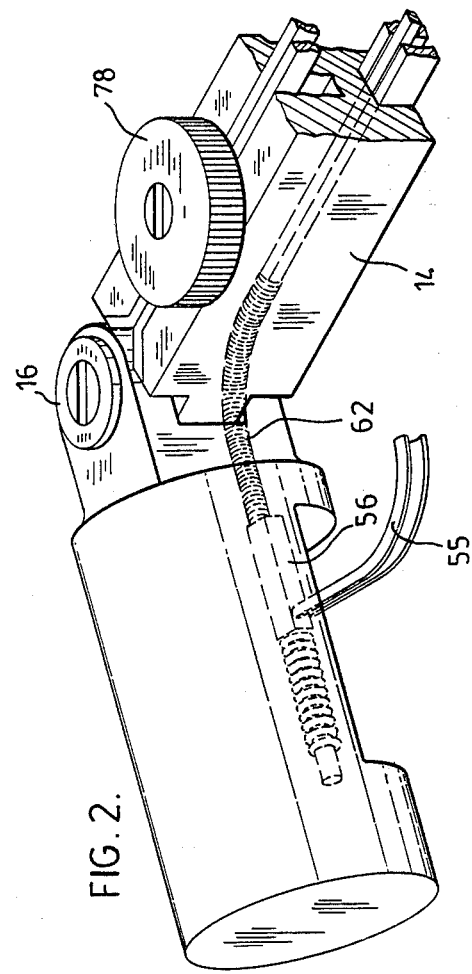
FIG. 2 is a detail perspective view of the hinge mechanism of the handle of the device of FIG. 1.
Figure 4:
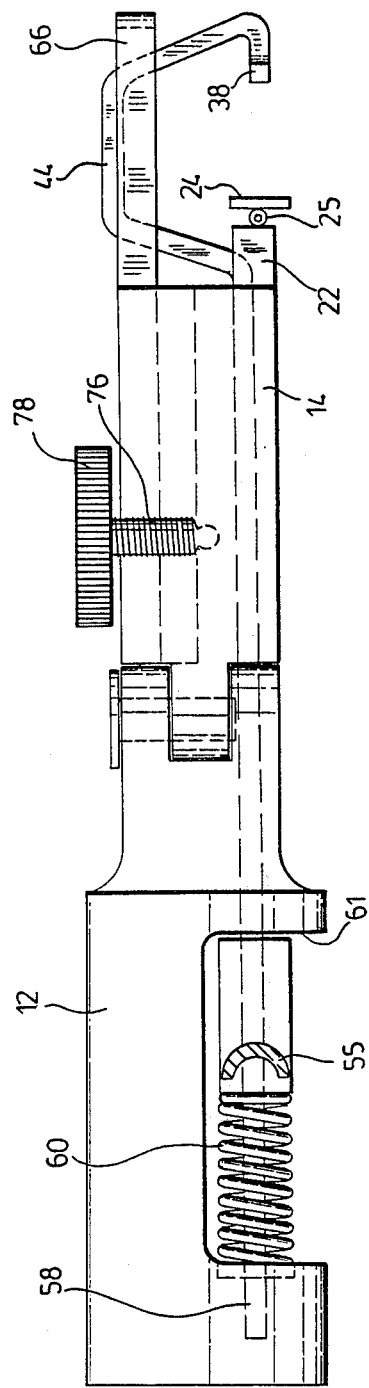
FIG. 4 is a side elevational view of the lingual placement device of FIG. 1 using the attachment holding means of FIG. 3.
Figure 5:
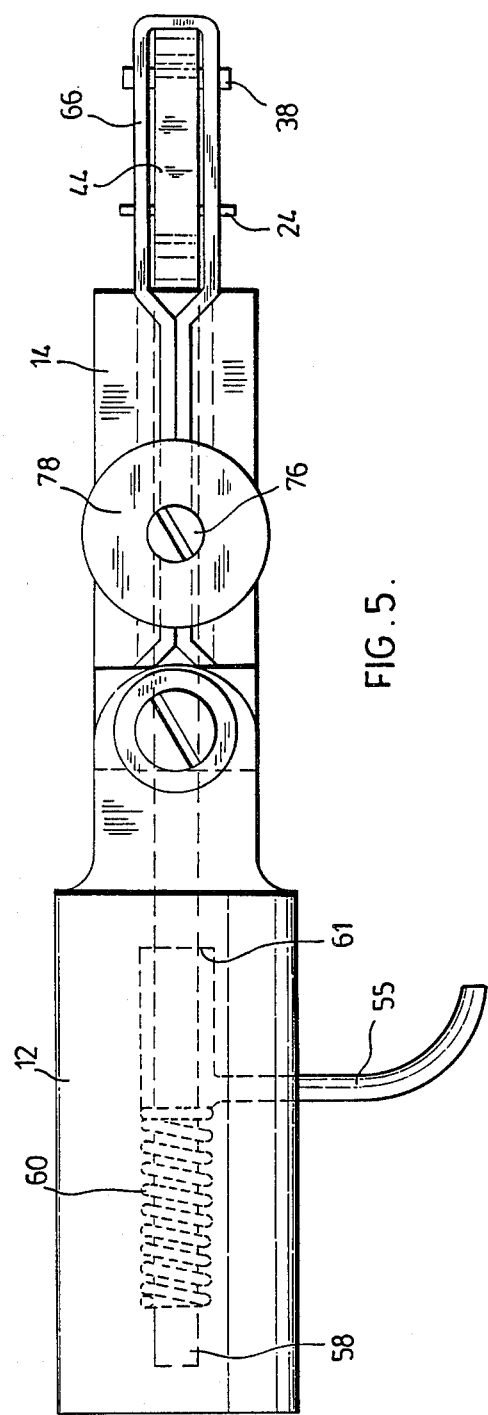
FIG. 5 is a plan view of the lingual placement device of FIG. 4.
Figure 6:
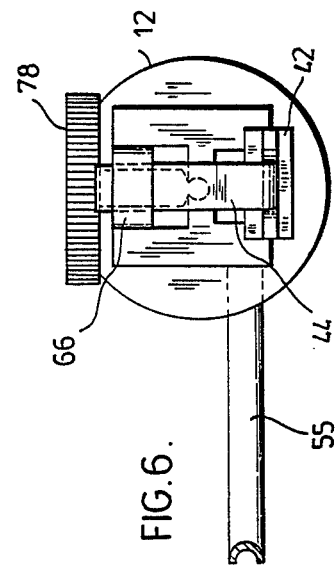
FIG. 6 is an end view of lingual placement device of FIG. 3.

Referring to the drawings, there is illustrated therein a lingual placement device 10 constructed in accordance with two embodiments of the invention, the embodiments differing in the construction of the orthodontic attachment holder. Those elements that are common to the two embodiments are identified by the same reference numerals.

The lingual placement device 10 comprises an elongate handle 12 which is hingedly connected to an elongate handle extension 14 for rotation about a vertically-extending pivot 16. The elongate handle extension 14 has a generally H-shaped cross section, defining a rectangularly-cross-sectioned upper recess 18 and a rectangularly-cross-sectioned lower recess 20.

Located in fixed position in the lower recess 20 are parallel elongate bars 22 which protrude forwardly from the recess 20. A tooth engaging plate 24 is mounted to the free ends of the bars 22 for rotation about a transversely-extending pivot 25, so that the plate 24 can rotate about a horizontal axis which is transverse to the axis of the handle extension 14.

Located in horizontally-spaced relationship with the tooth engaging plate 24 is an orthodontic attachment holder 26. As illustrated in FIG. 1, the attachment holder 26 comprises upper and lower jaw members 28 and 30 which are biased towards each other to grip the stringing tube 32 of an othodontic bracket 34.

As may be seen in FIG. 1, the orthodontic bracket 34 is positioned on the lingual side of a tooth 36 while the plate 24 engages the forward side of the tooth 36. The bracket 34 may be affixed to the lingual tooth face in any convenient manner, such as, by the use of an orthodontic cement or adhesive.

In the embodiment of FIG. 3, the orthodontic attachment holder 26 cómprises a horizontally-extending bar 38 of generally rectangular cross-section, dimensioned to be received in the stringing recess 40 of an orthodontic bracket 42.

The orthodontic attachment holder 26 is formed at one end of bridging or arching member 44 which arches over the tooth 36 when the device 10 is in use and enables the bracket 34 to be positioned on the lingual side of the tooth 36 by manipulation from outside the mouth of the patient without interference from the tooth 36 itself.

The bridging member 44 includes downwardly extending arms 46 and 48 joined by a horizontally-extending arm 50.

The downwardly-extending arm 46 terminates in the jaw member 28. An additional downwardly-extending arm 52 which terminates in the jaw member 30, is joined in abutting relation to arm 46 by means of a sleeve 53 which permits member 48 to move in vertical slideable relation to arm 46. This arrangement permits the jaw members 28 and 38 to open and close to release and grip the stringing tube 32.

The bridge member 44 is provided integral with one end of a push rod member 54 which extends in sliding relationship within the lower recess 20 between the bars 22. The push rod member 54 is operatively connected to an actuating lever 55 which is movable relative to the handle 12 to effect movement of the orthodontic attachment holder 26 towards and away from the tooth engaging plate 24.

The lever 55 is connected to a sleeve 56 which is slidably mounted on a bar 58 located in fixed position within the handle 12 and biased by a compression spring 60 towards the handle extension 14 and against a stop surface 61. The sleeve is joined to the push rod 50 by a flexible spring-loaded cable 62, or other suitable flexible connector which will permit rectilinear reciprocal movement to be transmitted from the lever 55 to the push rod 54 and thence to the orthodontic attachment holder 26, while still permitting pivoting of the handle extension 14 relative to the handle 12 about pivot 16.

Located in vertically-sliding relationship with the upper recess 18 is a base member 64 of an integral yoke member 66 which extends horizontally from the base member 64 and surrounds the upper portion of the bridge member 44, with the cross member 50 located above the yoke member 66.

The arms of the yoke member 66 engage the upper surface of the tooth 36 to aid in positioning the bracket 34.

The base member 64 comprises the integral extensions of the side arms of the yoke member 66, such extensions extending in face-abutting relationship to each other and terminating in diverging slots 70 adjacent the pivot 16. The base member 64 has a screw threaded opening 72 engaging the screw threads 74 of a vertically-extending rotatable bolt 76 having a knurled knob 78 integral therewith to effect rotation of the bolt 76.

Rotation of the knurled knob 78 causes the base member 64 to slide up or down, depending on the direction of rotation of the knob 78, in the slot 18. This movement, combined with the engagement between the arms of the yoke member 66, causes the orthodontic attachment holder 26 to move to a desired vertical location with reference to the tooth 36.

The jaws 28 and 30 of the orthodontic attachment holder 26 are biased together by a spring 80 which bears against a lever 82 which is integral with the upper end of the arm 52. Depression of the lever 52 causes the arm 52 to slide downwardly against the biasing of the spring 80 to open the jaws 28 and 30.

OPERATION

In operation of the device 10, an orthodontic bracket 34 is mounted to the attachment holder 26. After a dental cement is applied to the tooth-engaging surface of the bracket 34, the bridge member 44 is positioned over the tooth 36 to which it is desired to affix the bracket 34. The plate 24 is positioned in engagement with the front surface of the tooth while the arms of yoke 66 rest on top of the tooth 36. The pivot action of the plate 24 about pivot 25 enables the instrument 10 to be properly angled in any particular area of the mouth so that the bracket 34 can be properly positioned. The pivot action of the extension 14 relative to the handle 12 about pivot 16 enables access to both anterior and posterior teeth to be attained with ease.

Once the plate 24 has been positioned in engagement with the exterior surface of the desired tooth and the arms of the yoke 66 rest on top of the tooth 36, the knob 78 is rotated to establish the relative vertical position of the bracket 34 and the lingual tooth surface and the lever 55 is pulled to draw the bracket into engagement with the tooth surface, thereby gripping the tooth between the plate 24 and the bracket 34. Once the cement has cured sufficiently for the bracket 34 to adhere to the lingual tooth surface, the bracket 34 is released from the attachment holder 26 by depression of the lever 82, and the lever 55 is allowed to return to its original position under the influence of spring 60. The device 10 then is withdrawn from the mouth.

For the embodiment of FIG. 3, the operations involved are substantially the same as for the embodiment of FIG. 1 except that the instrument 10 is released from the positioned bracket 42 by moving the holder 38 away from the bracket 42 and out of the recess 40.

The instrument 10, therefore, is able to effectively and accurately position an orthodontic bracket at any desired location on the lingual side of any tooth in a patient's mouth, by simple and easily effected adjustments. The expense of the prior art transfer trays and time consuming nature of the operations resulting from the use thereof are overcome by the apparatus of the invention.

SUMMARY OF DISCLOSURE

In summary of this disclosure, the present invention provides a lingual placement device which is versatile in positioning orthodontic attachments in any desired location in the mouth of a patient. Modifications are possible within the scope of the invention.

What we claim is:

1. A lingual placement device for orthodontic attachments, comprising:
    tooth engaging means for engaging the forward side of a tooth,
    orthodontic attachment holding means for holding an orthodontic attachment in engagement with the lingual side of a tooth,
    means on said device for moving said attachment holding means in a horizontal direction towards and away from said tooth engaging means for bringing an orthodontic attachment into engagement with the lingual side of a tooth when said tooth engaging means is in engagement with the forward side of the tooth,
    means on said device for moving said attachment holding means in a vertical direction for positioning an orthodontic attachment in a desired vertical location with respect to the lingual side of a tooth when the tooth engaging means is in engagement with the forward side of the tooth, and
    handle means operatively connected to said tooth engaging means and to said attachment holding means.

2. The device of claim 1 wherein said handle means is operatively connected to said tooth engaging means and to said attachment holding means by handle extension means to which said tooth engaging means and said attachment holding means are mounted.

3. The device of claim 2 wherein said handle extension means is pivotally connected to said handle means for pivotal movement about a generally vertical axis.

4. The device of claim 2 or 3 wherein said tooth engaging means comprises a plate which is pivotally mounted to said handle extension means for movement about a generally horizontal axis extending transverse to the axis of the handle extension means, whereby said handle means and handle extension means may be moved upwardly or downwardly about said generally horizontal axis when said plate is in engagement with the forward side of a tooth.

5. The device of claim 2 or 3 wherein said attachment holding means is mounted to said handle extension means by a bridging member which bridges over the tooth, the lingual side of which the orthodontic attachment is to be attached, while the tooth engaging means is in engagement with the forward side of the tooth.

6. The device of claim 5 wherein said means for moving said attachment holding means in a vertical direction comprises second tooth engaging means engaging the upper surface of a tooth, said second tooth engaging means being operatively connected to said handle means and being movable vertically with respect to said handle means to permit movement of said handle and said attachment holding means upwardly and downwardly relative to said second tooth engaging means when the latter is in engagement with the surface of the tooth.

7. A lingual placement device for orthodontic attachments, comprising:

an elongate handle, an elongate handle extension pivotally connected to said elongate handle for pivotal movement of said handle extension about a generally vertical axis relative to said elongate handle, a tooth engaging plate mounted to said handle extension for pivotal movement about a generally horizontal axis extending generally transverse to the axis of the elongate handle extension, arch means extending from said handle extension and terminating in orthodontic attachment holding means spaced horizontally from said tooth engaging plate for engagement with a lingual side of a tooth while the tooth engaging plate engages the forward side of the same tooth, lever means mounted to said elongate handle for reciprocal movement axially of said elongate handle, means biasing said lever means towards said pivotal connection of said elongate handle to said elongate handle extension, means establishing operative connection between said elongate handle and said arch means and thereby said orthodontic attachment holding means, whereby movement of said lever means against the biasing of said biasing member causes said attachment holding means to move towards said tooth engaging plate for bringing an orthodontic attachment into engagement with the lingual side of a tooth when said tooth engaging plate is in engagement with the forward side of the tooth and movement of said lever means under influence of said biasing member causes said attachment holding means to move away from said tooth engaging plate to leave said orthodontic bracket in engagement with said lingual side of said tooth, and means on said device for moving said attachment holding means in a vertical direction for positioning an orthodontic attachment in a desired vertical location with respect to the lingual side of a tooth when the tooth engaging plate is in engagement with the forward side of the tooth.

8. The device of claim 7 wherein said means for moving said attachment holding means in a vertical direction comprises a yoke surrounding said arch means and mounted to said handle extension means for engagement with an upper surface of the tooth, and means for effecting vertical movement of said yoke relative to said handle extension means, whereby, engagement between said joke and said tooth causes vertical movement of the handle extension means, and thereby said attachment holding means upon actuation of said vertical movement effecting means.

9. The device of claim 8 wherein said elongate handle extension has a generally H-shaped cross section defining upper and lower channel-shaped recesses, said tooth engaging plate is mounted to said handle extension by means of a pair of elongate arm members which are mounted in spaced-apart relationship in said lower recess, extend from the forward end of said recess and have the tooth engaging plate mounted to the forward end of said arm extension, the operative connection between said lever means and said arch means includes an elongate bar-like member integrally joined at one end to said arch means and extending within said lower recess between said elongate arm members, said yoke mounted to said handle extension by being cantilevered from an elongate support member slidably mounted in said upper recess, and said means for effecting vertical movement of said yoke comprises a threaded bore in said elongate support member, a threaded bolt threadedly-engaged in said bore and means for rotating said threaded bolt to cause sliding vertical movement of said support member in said upper recess.

10. The device of claim 7, 8, or 9 wherein said orthodontic attachment holding means comprises a pair of jaw members biased towards each other to grip a threading tube of an orthodontic bracket therebetween, and means for opening said jaw member against said biasing to effect release of said orthodontic bracket.

11. The device of claim 7, 8 or 9 wherein said orthodontic attachment holding means comprises a rectangularly cross-sectioned bar dimensioned to be received in the stringing recess of an orthodontic bracket.

* * * * *

UNITED STATES PATENT AND TRADEMARK OFFICE
CERTIFICATE OF CORRECTION

PATENT NO. : 4,424,029
DATED : January 3, 1984
INVENTOR(S) : Rolf Maijer et al.

It is certified that error appears in the above-identified patent and that said Letters Patent is hereby corrected as shown below:

On the title page, /73/ Assignee: should read
-- Romada Holdings Ltd. ---.

"Attorney, Agent or Firm" should read
-- Sim & McBurney --,

Signed and Sealed this

Tenth Day of July 1984

[SEAL]

Attest:

GERALD J. MOSSINGHOFF

Attesting Officer   Commissioner of Patents and Trademarks